(12) United States Patent
Chang et al.

(10) Patent No.: US 6,616,784 B2
(45) Date of Patent: Sep. 9, 2003

(54) METHOD FOR FABRICATING TRANSMISSION ELECTRON MICROSCOPE

(75) Inventors: Wen-Tung Chang, Hsinchu (TW); Hsing-Shuang Chou, Hsinchu Hsien (TW)

(73) Assignee: United Microelectronics Corp., Hsinchu (TW)

( * ) Notice: Subject to any disclaimer, the term of this patent is extended or adjusted under 35 U.S.C. 154(b) by 0 days.

(21) Appl. No.: 09/832,704

(22) Filed: Apr. 11, 2001

(65) Prior Publication Data
US 2002/0104612 A1 Aug. 8, 2002

(30) Foreign Application Priority Data
Feb. 6, 2001 (TW) ........................ 90102494 A

(51) Int. Cl.[7] ............................... G01N 1/28; G01N 1/32
(52) U.S. Cl. .................... 156/154; 156/249; 156/250; 250/307; 250/311; 250/440.11
(58) Field of Search ................... 250/440.11, 307, 250/311; 156/249, 154, 250

(56) References Cited

U.S. PATENT DOCUMENTS

| 5,256,463 A | * | 10/1993 | Osaka et al. | 156/264 |
| 5,372,987 A | * | 12/1994 | Fisch et al. | 428/195 |
| 5,572,026 A | * | 11/1996 | Ikeda | 250/307 |
| 5,783,519 A | * | 7/1998 | Morrison et al. | 428/195 |
| 5,840,215 A | * | 11/1998 | Iyer et al. | 156/247 |
| 6,194,720 B1 | * | 2/2001 | Li et al. | 250/311 |
| 6,394,409 B1 | * | 5/2002 | Chen et al. | 248/694 |
| 6,420,722 B2 | * | 7/2002 | Moore et al. | 250/559.27 |

* cited by examiner

Primary Examiner—Mark A. Osele
(74) Attorney, Agent, or Firm—J. C. Patents

(57) ABSTRACT

A fabrication method for a transmission electron microscope (TEM) slide is described. A die having device structures formed thereon is provided. A thermal adhesive fills the surface of device structures formed on the die. The thermal adhesive is covered by a glass piece. A polishing step is performed to a non-device side of the die to form a thin sheet from the die. The glass piece is removed to expose the thermal adhesive. A sacrificial layer is then formed above the exposed thermal adhesive on the thin sheet. A slicing step is performed to form a TEM slide from the thin sheet.

16 Claims, 2 Drawing Sheets

US 6,616,784 B2

METHOD FOR FABRICATING TRANSMISSION ELECTRON MICROSCOPE

CROSS-REFERENCE TO RELATED APPLICATION

This application claims the priority benefit of Taiwan application serial no. 90102494, filed Feb. 6, 2001.

BACKGROUND OF THE INVENTION

1. Field of the Invention

The present invention relates to a method for fabricating a slide. More particularly, the present invention relates to a method for fabricating a transmission electron microscope slide..

2. Description of the Related Art

Cross sectional analysis is considered an effective technology in the failure analysis of very large semiconductor integrated (VLSI) devices. Scanning electron microscopes (SEM) are instruments used in cross sectional observation. However, where device density is very high, the resolution of scanning electron microscopes tends to be very poor. Thus, as fabrication processes gradually enter the VLSI stage, scanning electron microscopes have been gradually replaced by transmission electron microscopes (TEM). In order to resolve problems related to yield and device dependability; the use of TEM to perform failure analysis has become more and more prevalent.

In present-day, advanced copper fabrication processes, a barrier layer, used to prevent the diffusion of copper particles, is often formed in via holes, trench openings and damcene openings. Afterwards, the barrier layer is then covered with a copper-seed (Cu-seed) layer. The step-coverage quality of the barrier layer and Cu-seed layer affects the quality of the subsequently formed metal plug and the conductive line. Thus, it necessary to make use of cross-sectional analysis technology to determine whether or not the quality of the barrier layer and Cu-seed layer conform to given standard That is to say, cross-sectional analysis is used to determine whether the step-coverage quality and thickness of the barrier and Cu-seed layers are acceptable, in order to raise operational effectiveness and dependability, as well as to raise yield and lower fabrication costs.

The openings observed under a conventional transmission electron microscope are generally filled with platinum, tungsten nitride or an oxide material. These materials are used to provide a dependable support structure as well as to provide a greater contrast when viewed through the TEM microscope. The greater contrast makes it possible to determine clearly whether or not the barrier layer and Cu-seed layers have been formed well.

However, if platinum or tungsten is used as a filler material, the platinum and tungsten appear as a dark image when the quality and thickness of the barrier layer and Cu-seed layer are observed under the TEM. The lack of contrast between the Cu-seed layer and the barrier layer makes it extremely difficult to discern the two layers.

Moreover, when chemical vapor deposition is conducted in the opening to form a filler of oxide material or nitride material, the Cu-seed layer melts as a result of the high temperature which causes Cu-agglomeration. The melting of the Cu-seed layer can occur even when a low-temperature deposition process (300° C.), such as plasma enhanced CVD, PECVD, is performed. It then becomes impossible to determine clearly the actual thickness of the Cu-seed layer from the image under the TEM, which would impair the inspection.

SUMMARY OF THE INVENTION

Accordingly, the present invention provides a fabrication method for a TEM slide. The method comprises providing a die. A thermal adhesive is deposited over a surface of several device structures formed on the die. The thermal adhesive is covered by a glass piece. A polishing step is conducted to a non-device side of the die to form a thin sheet from the die. The glass piece is then removed, to expose the thermal adhesive. A layer comprising sacrificial material is then formed above the exposed thermal adhesive on the thin sheet. An ion transmission step is then conducted to form a TEM slide from the thin sheet.

As embodied and broadly described herein, a TEM slide fabrication method is provided, according to a preferred embodiment of the present invention, wherein the glass transition temperature of the thermal adhesive is approximately 90°–100° C. and the approximate temperature of the thermal adhesive covering the die is about 90°–100° C.

The glass transition temperature of the thermal adhesive is approximately between 90°–100° C. This temperature is lower, in relation to the temperature of plasma enhanced CVD and the melting point of metal. The low-temperature thermal adhesive used to fill openings prevents the thermal adhesive from damaging the crystal seed layer. In the case where the seed layer is a Cu-seed layer, Cu-agglomeration can be avoided.

Additionally, the thermal adhesive when viewed under the TEM electron microscope provides excellent contrast. Thus, the profile of the stacked layer can be clearly distinguished, which increases the accuracy of inspection results.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention, and, together with the description, serve to explain the principles of the invention. In the drawings.

DESCRIPTION OF THE PREFERRED EMBODIMENTS

Figure 1:
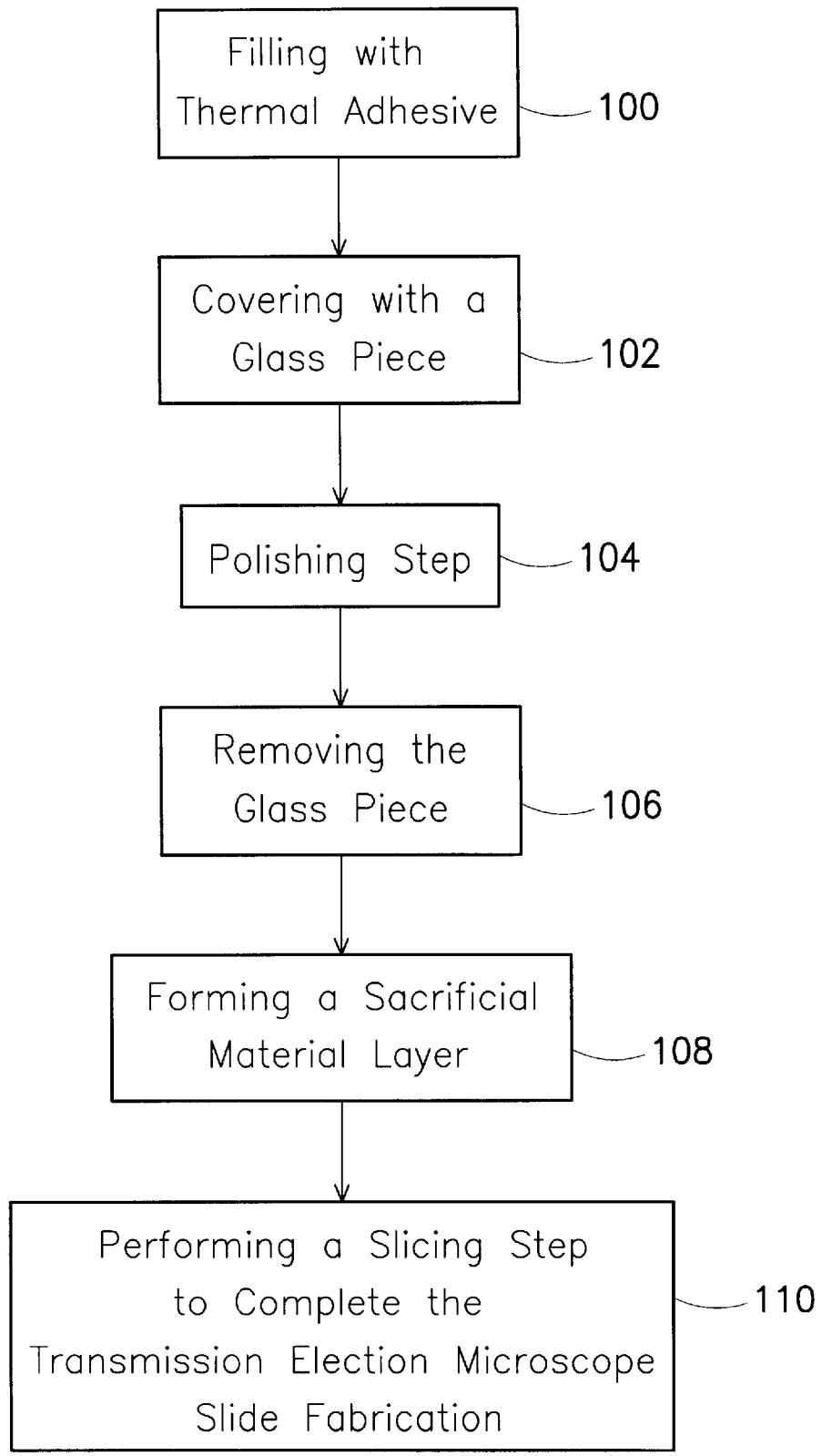
FIG. 1 is a flow diagram illustrating the fabrication of a transmission electron microscope (TEM) slide according to one preferred embodiment of this invention.
Figure 2:
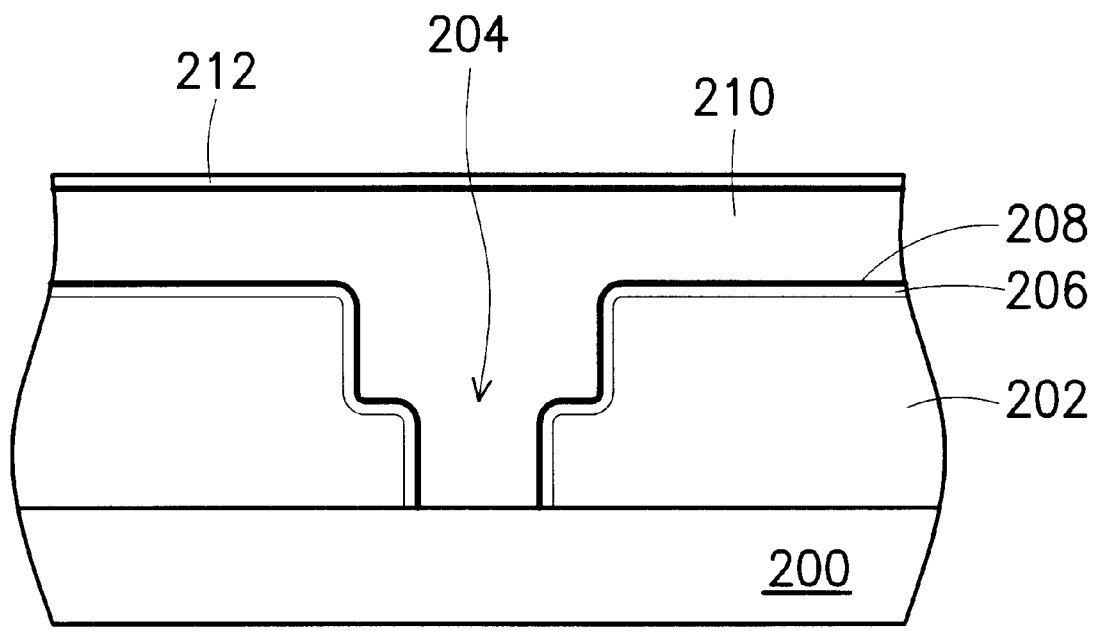
FIG. 2 is a schematic drawing illustrating a microscope slide according to a preferred embodiment of this invention.

FIG. 1 is a flow diagram illustrating the fabrication of a transmission electron microscope (TEM) slide according to one preferred embodiment of this invention. FIG. 2 is a schematic drawing illustrating a microscope transmission electron microscope (TEM) slide according to a preferred embodiment of this invention.

As shown in FIG. 1, a die is provided. Several devices and openings are formed on the die. A stacked structure is formed on the surface of the openings. This stacked structure, which can be made of copper for example, comprises a barrier layer and a crystal seed layer formed above the barrier layer. As shown in FIG. 2, a slide of a damascene opening observed under a TEM microscope is used as an example. The aforementioned barrier layer and crystalline seed layer are layers 206 and 208 of FIG. 2 respectively. The barrier layer 206 is, for example, a tantalum-nitride-tantalum (TNT) layer formed by physical vapor deposition. The crystal seed layer is, for example, a Cu-seed layer formed by physical vapor deposition.

A thermal adhesive layer is formed over the die (as shown in step 100 of FIG. 1 and step 210 of FIG. 2). The thermal adhesive layer completely fills the opening in the die (as illustrated by opening 204 of FIG. 2). The method of covering die with a thermal adhesive and filling the opening includes a gravitational acceleration method. The glass transition temperature of the thermal adhesive is approximately between 90° and 100° C. That is to say, the temperature required in the process of covering the die and filling the openings is approximately between 90° and 100° C.

The temperature of the thermal adhesive is lower, relative to the temperature of the plasma enhanced chemical vapor deposition method and the melting point of metal. Thus, the low-temperature thermal adhesive used to fill openings in the die prevents the thermal adhesive from damaging the crystal seed layer. In the case where the seed layer is a Cu-seed layer, Cu-agglomeration can be avoided. Cu-agglomeration makes it difficult to accurately measure the thickness of the Cu-seed layer and to judge step-coverage quality, when inspected under a TEM.

Additionally, the thermal adhesive when viewed through the transmission electron microscope provides very good contrast. Thus, the stacked layer profile can be discerned very clearly. Consequently, the accuracy of inspection results can be raised.

As shown in step 102 of FIG. 1, a glass piece is placed over the thermal adhesive. The glass piece, used to protect the die, can be a glass slide, for example. Polishing step 104 is performed to polish the non-device side of the die to form a thin sheet. The approximate thickness of the thin sheet is between 20–30 microns.

After the step of polishing the die has been completed, the glass piece above the thin sheet is removed (as shown in step 106 of FIG. 1), to expose the surface of the thermal adhesive. A layer comprised of sacrificial material is then formed on the exposed thermal adhesive on the thin sheet (as shown in step 108 of FIG. 1 and layer 212 in FIG. 2). This sacrificial layer serves to protect the thin sheet as well as prevent the accumulation of electrical charge in the subsequent slicing process. The sacrificial material can be platinum with a thickness of 1–3 microns.

The slicing step 110 is then performed to form a transmission electron microscope slide. The slicing step can be performed using a focus ion beam (FIB), for example.

As shown in FIG. 2, a slide of a damascene opening observed under a TEM microscope is used as an example. A stacked layer having a barrier layer 206 and a crystal seed layer 208 is formed above the dielectric layer 202 of the damascene opening 204. A thermal adhesive layer 210 is then formed above the crystal seed layer 208. The thermal adhesive layer 210 also fills the damascene opening. A sacrificial layer 212 is then formed above the thermal adhesive layer 210.

In the present invention, the glass transition temperature of the thermal adhesive layer is approximately between 90° and 100° C. Thus, the low-temperature thermal adhesive used to fill openings in the die prevents the thermal adhesive from damaging the crystal seed layer. In the case where the seed layer is a Cu-seed layer, Cu-agglomeration can be avoided. Cu-agglomeration makes it difficult to accurately measure the thickness of the Cu-seed layer and to judge the quality of the layer, when inspected under a TEM.

Additionally, the thermal adhesive when viewed through the transmission electron microscope provides very good contrast. Thus, the stacked layer profile can be discerned very clearly. Consequently, the accuracy of inspection results can be raised.

The embodiments of the present invention are illustrated using a slide of a damascene opening observed under a TEM microscope as an example. However, the actual use of the present invention is not merely limited to the inspection of damascene openings. The present invention can also be used to inspect contact openings, via openings, conductive trenches.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A fabrication method for a transmission electron microscope (TEM) slide, comprising:

Providing a die;

Covering a surface of device structures formed on the die with a thermal adhesive;

Covering the thermal adhesive with a glass piece;

Performing a polishing step to a non-device side of the die to form a thin sheet from the die;

Removing the glass piece above the thin sheet to expose the thermal adhesive;

Forming a layer comprising sacrificial material above the exposed thermal adhesive on the thin sheet; and Performing a slicing step to form a TEM slide from the thin sheet.

2. The method of claim 1, wherein an approximate temperature of the thermal adhesive covering the die is between 90°–100° C.

3. The method of claim 1, wherein the glass piece includes a glass slide.

4. The method of claim 1, wherein an approximate thickness of the thin sheet is about 20 microns to about 30 microns.

5. The method of claim 1, wherein a material of the sacrificial layer includes platinum layer.

6. The method of claim 1, wherein the method used to cover the die with a thermal adhesive includes a gravitational acceleration method.

7. The method of claim 1, further including forming a barrier layer over a surface of several openings, which have been formed above the die.

8. The method of claim 7, further including forming a crystal seed layer above the barrier layer.

9. The method of claim 8, wherein the crystal seed layer includes a Cu-seed layer.

10. The method of claim 1, wherein the slicing step includes using a focus ion beam.

11. A fabrication method for a transmission electron microscope (TEM) slide, comprising:

providing a die upon which a plurality of devices and openings have been formed, wherein a barrier layer and a crystal seed layer are sequentially formed on a surface of the openings;

performing a gravitational acceleration step to form a thermal adhesive over the die, wherein the thermal adhesive completely fills the openings;

covering the thermal adhesive with a glass piece;

performing a polishing step to a non-device side of the die to form a thin sheet from the die;

removing the glass piece above the thin sheet to expose the thermal adhesive;

covering the exposed thermal adhesive on the thin sheet with a layer comprising sacrificial material; and performing a slicing step to form a TEM slide from the thin sheet.

12. The method of claim 11, wherein an approximate temperature for performing a gravitational acceleration step to form the thermal adhesive covering the die is about 90° to about 100° C.

13. The method of claim 11, wherein the glass piece includes a glass slide.

14. The method of claim 11, wherein an approximate thickness of the thin sheet is between 20–30 microns.

15. The method of claim 11, wherein a material of the sacrificial layer includes platinum layer.

16. The method of claim 11, wherein the crystal seed layer includes a Cu-seed layer.

* * * * *